(12) United States Patent
Sastry

(10) Patent No.: US 8,877,185 B2
(45) Date of Patent: Nov. 4, 2014

(54) MANAGING AND TREATING KELOIDS

(76) Inventor: Stan S. Sastry, Mill Creek, WA (US)

(*) Notice: Subject to any disclaimer, the term of this patent is extended or adjusted under 35 U.S.C. 154(b) by 0 days.

(21) Appl. No.: 13/506,690

(22) Filed: May 10, 2012

(65) Prior Publication Data

US 2012/0263705 A1    Oct. 18, 2012

(51) Int. Cl.
| | |
|---|---|
| *A61K 33/44* | (2006.01) |
| *A61K 31/58* | (2006.01) |
| *A61K 31/165* | (2006.01) |
| *A61K 36/185* | (2006.01) |

(52) U.S. Cl.
CPC ............. *A61K 31/58* (2013.01); *A61K 31/165* (2013.01); *A61K 33/44* (2013.01); *A61K 36/185* (2013.01)
USPC ........................................ 424/125

(58) Field of Classification Search
None
See application file for complete search history.

(56) References Cited

U.S. PATENT DOCUMENTS

| | | | |
|---|---|---|---|
| 5,500,409 A | 3/1996 | Tan et al. | |
| 5,895,056 A | 4/1999 | Habuta et al. | |
| 6,348,501 B1 | 2/2002 | Holt et al. | |
| 6,503,246 B1 | 1/2003 | Har-Shai et al. | |
| 6,569,838 B1 | 5/2003 | Hellerqvist et al. | |
| 6,573,302 B1 | 6/2003 | Holt et al. | |
| 6,593,370 B2 | 7/2003 | Tamura et al. | |
| 6,664,287 B2 | 12/2003 | Avery et al. | |
| 7,053,050 B2 | 5/2006 | Yasuda et al. | |
| 7,300,916 B2 | 11/2007 | Yasuda et al. | |
| 7,399,783 B2 | 7/2008 | Rosenbloom | |
| 7,700,076 B2 | 4/2010 | Tamarkin et al. | |
| 7,871,647 B1 * | 1/2011 | Paradise | 424/725 |
| 7,951,393 B2 | 5/2011 | Harris | |
| 8,048,918 B2 | 11/2011 | Ward et al. | |
| 8,052,983 B2 | 11/2011 | Ashley | |
| 8,057,802 B2 | 11/2011 | Gomer et al. | |
| 8,063,263 B2 | 11/2011 | Gurtner et al. | |
| 8,071,140 B2 | 12/2011 | Hill | |
| 8,110,576 B2 | 2/2012 | Ibrahim et al. | |
| 2001/0038846 A1 | 11/2001 | Brown | |
| 2004/0043026 A1 | 3/2004 | Tuan | |
| 2005/0239755 A1 | 10/2005 | Kawazoe et al. | |
| 2008/0038381 A1 | 2/2008 | Le et al. | |
| 2009/0305279 A1 | 12/2009 | Ferguson et al. | |
| 2010/0184610 A1 | 7/2010 | Fergusin et al. | |

(Continued)

OTHER PUBLICATIONS

Website entitled "Cordran (Flurandrenolide) tape" dated May 2008; http://dailymed.nlm.nih.gov/dailymed/archives/fdaDrugInfo.cfm?archiveid=8339.*

(Continued)

*Primary Examiner* — Alissa J Prosser
(74) *Attorney, Agent, or Firm* — Stan S. Sastry; The Law Office of Stan Sastry PLLC

(57) ABSTRACT

Methods of managing and treating a keloid in mammal are disclosed. An embodiment includes managing and treating a keloid by covering the keloid with flurandrenolide tape, applying graphites ointment on the keloid and applying witch hazel ointment on the keloid. A further embodiment includes covering the keloid with flurandrenolide tape; and removing the flurandrenolide tape from the keloid after 5 to 10 hours; and applying witch hazel ointment on the keloid; and applying capsaicin ointment on the keloid. Yet another embodiment comprises steps of making and providing a mixture including equal proportions by mass (or weight) of flurandrenolide, witch hazel, graphites and capsaicin; and applying the mixture on the keloid in a manner that includes covering the keloid with the mixture.

2 Claims, 12 Drawing Sheets

(56) References Cited

U.S. PATENT DOCUMENTS

| | | | |
|---|---|---|---|
| 2011/0008312 A1 | 1/2011 | Suzuki et al. |
| 2011/0319408 A1 | 12/2011 | Kim et al. |
| 2012/0004252 A1 | 1/2012 | Ebe et al. |
| 2012/0009146 A1 | 1/2012 | Gomer et al. |
| 2012/0035521 A1 | 2/2012 | Zepeda et al. |
| 2012/0035674 A1 | 2/2012 | Weinstock |
| 2012/0035688 A1 | 2/2012 | Hancock |

OTHER PUBLICATIONS

Kelly "Update on the Management of Keloids," Seminars in Cutaneous Medicine and Surgery 28:71-76, 2009.*
Website entitled "Rubbing Alcohol & Hydrogen Peroxide" dated Mar. 2011; http://www.livestrong.com/article/181945-rubbing-alcohol-hydrogen-peroxide/.*
Website entitled "Types Eczema Treatment" dated Jan. 2010; http://carcinomacells.blogspot.com/2010/01/eczema-treatment.html.*
Website entitled "Flurandreolide topical cream" dated Apr. 2009; http://health.yahoo.net/goldcontent/flurandrenolide.*
Read, "Treatment of Keloid Scarring," British Journal of Sexual Medicine, pp. 10-12, Jan. 1981.*
The online Skin Care Guide article "Removing Scars: graphites" dated Oct. 10, 2010; http://www.skincareguide.com/article/removing-scars-graphites.html.*
Google search page showing date of "Removing Scars: graphites" as Oct. 10, 2010, printed 2013.*
Ameghino "Healing powers" dated Mar. 23, 1999; http://www.theguardian.com/lifeandstyle/1999/mar/23/healthandwellbeing.health.*
The online guidelines "Post Operative Homeopathic Prescribing" dated Aug. 7, 2007; http://www.h2rc2.com/cancer/resources/Holistic-Healing/Homeopathy/PostSurgPrescribing.pdf.*
Google search page showing date of "Post Operative Homeopathic Prescribing" as Aug. 7, 2007, printed 2013.*
The online article "Haelan cream/ointment: how does it work?" dated Nov. 15, 2010; http://www.netdoctor.co.uk/skin-and-hair/medicines/haelan-cream-and-ointment.html.*
Google search page showing date of "Haelan cream/ointment" as Nov. 15, 2010, printed 2013.*
The CAS registry entry for "flurandrenolide" 2013.*
Wang, Haibin and Lao, Shengkang Establishment of an animal model for human keloid scars using tissue engineering method. Journal of Burn Care and Research Dec. 28, 2012.US.
Maria L. C. Ramos, Alfredo Gragnani and L.M. Ferreira Is there an ideal animal model to study hypertrophic scaring? Journal of Burn Care and Research 2008; 29:363-368 USA.
Faten A. Khorshid Comparative study of keloid formation in humans and laboratory animals. Med Sci Monit, 2005; 11(7): BR212-219; Med Sci Monit, 2005; 11(7): BR212-219; BR.
Wesite title: Fibromyalgia, date of publication: Oct. 28, 2009. http://www.ncbi.nlm.nih.gov/pubmedhealth/PMH0001463/.
What is eczema? What causes eczema?; date of publication Jul. 20, 2009. http://www.medicalnewstoday.com/articles/14417.php.

* cited by examiner

MANAGING AND TREATING KELOIDS

FIELD OF THE INVENTION

This invention is generally related to the field that includes treatment methods for skin conditions such as keloids, hypertrophic scars and other skin disorders.

BACKGROUND

Keloids are a type of skin scar that is usually characterized by a raised skin surface of irregular appearance, smooth, soft or hard to the touch and irritation. Keloidation may potentially occur in any part of the skin, but keloids are generally seen on the chest, neck, jaws, shoulders, thighs and arms. It is thought that keloidation usually starts after injury to the skin. Keloidation is caused by excessive collagen deposition in the skin. Keloids are benign and are not generally a serious health risk. However, keloids are cosmetically unsightly, especially on exposed parts of the skin. Some keloids are of health concern because they may cause excessive itching, irritation and pain, particularly when they are abrasive against clothing. Keloids are thought to more frequently occur in human populations of high melanin content. Keloids generally start as small pimples or scars following wound healing and then spread continuously but slowly over very long periods of time. In many cases, keloids enter a static growth period after achieving a certain undeterminable size. Keloids, in general, do not spontaneously recede in size, nor do they disappear permanently without medical intervention.

Therapeutic intervention and management of keloids remains challenging because effective treatment options are limited. Keloids are treated either by the external use of drugs and chemicals, or by surgery (in usually difficult cases) or by radiation. Most treatment regimes yield limited positive results in terms of long-term prognosis. Surgical excision of keloids is generally not a preferred treatment option because keloids usually grow back, often with a vengeance that may make the patient feel worse. Some chemical and allied methods of treatment and management of keloids includes, but not limited to, localized corticosteroid injections, and freezing and thawing in combination with corticosteroid use, silicone gel and silicone occlusive sheeting, application of localized pressure, radiation therapy, interferon therapy, laser therapy. Despite the use of the foregoing therapies (and some others) there is currently no permanent "magic-bullet" for the treatment or cure of keloids. The present invention endeavors to treat and manage keloids by reducing the thickness and flattening out the keloid to a level that results in reduction in pain and irritation and redness. By permanently reducing the thickness of keloidal scars, the associated pain from a persistent keloid, the cosmetic appearance of skin and the body-image of a patient may be significantly improved.

SUMMARY OF THE INVENTION

Embodiments of methods of treating a keloid in a mammal are described. An embodiment of the methods of treating a keloid comprises one or more steps of covering the keloid with flurandrenolide tape. Flurandrenolide tape is applied by using a sticky side of the tape on top of a keloid and pressing the tape against the keloid until the tape adheres to the surface of the keloid. The flurandrenolide tape is held to stay for at least 5-10 hours, whereupon the tape is removed and the keloid is washed with soap and water and is dried. In one embodiment, graphites ointment is applied on the keloid so as to cover the keloid. In an embodiment the graphites is left overnight to soak into the keloid. In another embodiment, capsaicin ointment is applied on the graphites-covered keloid. The capsaicin ointment is thoroughly massaged on to the keloid by rubbing with a finger, for example. In one embodiment, a capsaicin-graphites ointment mixture is applied on a keloid and allowed to soak into the keloid overnight.

A method of treating a keloid, wherein the keloid is firstly cleaned with water and soap and dried. The keloid is secondly cleaned with either rubbing alcohol or ethyl alcohol and dried.

In an embodiment, the keloid is covered with flurandrenolide tape by firmly attaching the flurandrenolide tape to the keloid in a manner that completely covers the keloid. The tape is allowed to stay attached to the keloid from morning till evening (at least 5-10 hours). In yet another embodiment, the flurandrenolide tape is removed from the keloid, following which, the keloid is firstly washed with soap and water and secondly the keloid is dried. In another embodiment, graphites ointment is applied in a manner that includes completely or partially covering the keloid with the graphites ointment. In a further embodiment, witch hazel ointment is applied in a manner that includes covering the keloid that has been covered with the graphites ointment. In an embodiment, the witch hazel ointment is thoroughly massaged into the keloid by rubbing the witch hazel ointment with a finger, for example. In another embodiment, capsaicin ointment is applied in a manner that includes covering the keloid with the graphites ointment. In yet another embodiment, the capsaicin ointment is applied to the keloid that has been already covered with witch hazel ointment and graphites ointment. In a further embodiment, graphites ointment and witch hazel ointment and capsaicin ointment are successively and repeatedly applied to a keloid until a thickness and/or toughness of the keloid is reduced to a level of comfort/tolerance for a patient. In an embodiment, a method of treating a keloid comprises repeated daily applications of graphites ointment and witch hazel ointment and capsaicin ointment over a period of many years in order to achieve a level of reduction in thickness, toughness, redness and irritation of the keloid.

In an embodiment, a method of treating a keloid in a mammal comprises one or more steps that include: covering the keloid with flurandrenolide tape; and applying witch hazel ointment on the keloid; and then applying capsaicin ointment on the keloid. In a different embodiment, the flurandrenolide tape is used to cover the keloid all day. Following removal of the tape at night or evening, a patient cleans a keloid with soap and water and the keloid is dried. In yet another embodiment, witch hazel ointment is applied on the keloid; and then capsaicin ointment is applied on the keloid. The witch hazel and capsaicin are allowed to soak into the keloid overnight by rubbing the witch hazel and the capsaicin with a finger.

In an embodiment, a method of treating a keloid in a mammal comprises one or more steps that include: covering the keloid with flurandrenolide; and applying graphites ointment on the keloid; and then applying capsaicin ointment on the keloid.

In a different embodiment, a flurandrenolide tape is used to cover a keloid all day. Following removal of the tape at night or evening, the keloid is cleaned with soap and water and the keloid is dried. In yet another embodiment, graphites ointment is applied on the keloid; and then capsaicin ointment is applied on the keloid. The graphites and capsaicin are allowed soak into the keloid overnight by rubbing the graphites and the capsaicin with a finger.

An embodiment of a method of treating a keloid in a mammal includes, making and providing a mixture of equal proportions by mass (or weight) of flurandrenolide, witch hazel, graphites and capsaicin. In another embodiment the method further includes applying the mixture on the keloid in a manner that includes covering the keloid with the mixture and rubbing the mixture in to the keloid by massaging the keloid with a finger. In yet another embodiment, the mixture is allowed to soak into the keloid overnight.

An embodiment of a method of treating a keloid in a mammal includes making and providing a mixture of equal proportion by mass (or weight) of flurandrenolide, witch hazel, graphites and capsaicin. This mixture is applied repeatedly on the keloid until the keloid is reduced in thickness and size. In a further embodiment of the method of treating a keloid in a mammal, the mixture of equal proportion of flurandrenolide, witch hazel, graphites and capsaicin is applied repeatedly on the keloid until the keloid is reduced in thickness and size to a level of comfort for the mammal.

An embodiment of a method of treating a keloid in a mammal includes making and providing a mixture of an equal proportion by mass (or weight) of witch hazel, graphites and capsaicin. The mixture is applied repeatedly on the keloid until the keloid is reduced in thickness and size. In a further embodiment of the method of treating a keloid in a mammal, the mixture of equal proportion of witch hazel, graphites and capsaicin is applied repeatedly on the keloid until the keloid is reduced in thickness and size to a level of comfort for the mammal.

In addition to the foregoing, other aspects are described in the claims, drawings or photographs, tables and text forming a part of the present disclosure. Furthermore, various other methods and treatment regimen and management aspects are set forth and described in the teachings such as text (e.g., claims and/or detailed description) and/or drawings or photographs of the present disclosure.

The foregoing summary is illustrative only and is not intended to be in any way limiting. In addition to the illustrative aspects, embodiments, and methods described above, further aspects, embodiments, and methods will become apparent by reference to the drawings or photographs or tables and the detailed description.

DETAILED DESCRIPTION

In the following detailed description, reference is made to the accompanying drawings, photographs and tables, which form a part hereof The illustrative embodiments described in the detailed description, drawings, photographs or tables and claims are not meant to be limiting. Other embodiments may be utilized, and other changes may be made, without departing from the spirit or scope of the subject matter presented here.

EXAMPLE 1

Figure 1:
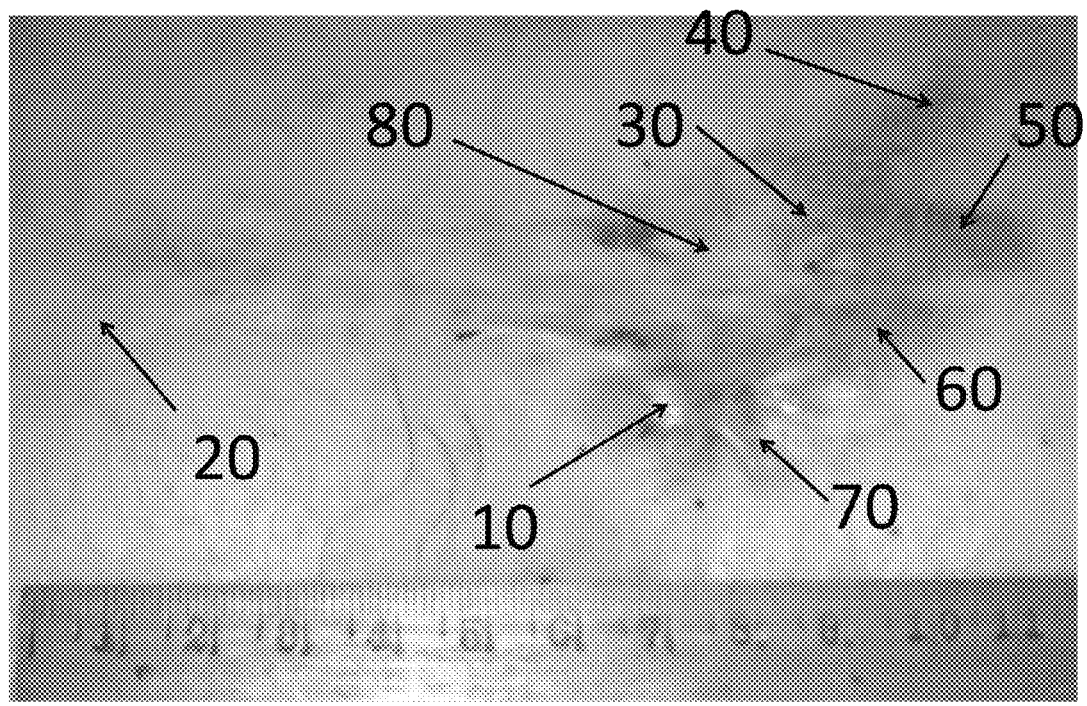
FIG. 1 is an exemplary photograph of a large keloid.

The following disclosure is drawn to methods of treating or managing a keloid or scar or other hypertrophic skin growth. FIG. 1 is an illustrative example of a large keloid on a patient's chest. This keloid has been in existence for at least 30 years. It started as a small scar left after a superficial wound had healed. The original scar on this patient was around the area denoted as 10. The scar grew over an approximate time period of 30 years into its current shape and form shown in FIG. 1. For the first 10-15 years the growth of the keloid was steady increased towards the area designated 30. Thus the region between 10 and 30 is considered the oldest and the most toughly fibrous region of the keloid. After about 15 years of slow and steady growth between the denoted 10-30 area, the keloid growth began to spread albeit slowly towards region designated 20 in FIG. 1. Currently, as of 2012, there has been no growth past the area 20. However, over the past 10 years or so, there have been finger-like growths starting with 40 and 50 and additional growth at 60 and 70. As it stands, the keloid is appears to have gone into an arrested state and no new growth has occurred during the past 3-5 years. The approximate size of the keloid is currently length-wise about 12 cm (or about 4.5 inches) as measured lengthwise from area 20 to area 50 in FIG. 1. The thickness of the keloid varies from area 20 to area 50. For the past 10-15 years the area 20 is the thinnest part of the keloid, since it is most nascent growth area. The thickest and the most raised area of the keloid is the area designated 10-80. Area 10-80 is also the firmest and the toughest part of the keloid, and hence the thickness measurements were made at and around area 10-80.

Figure 2:
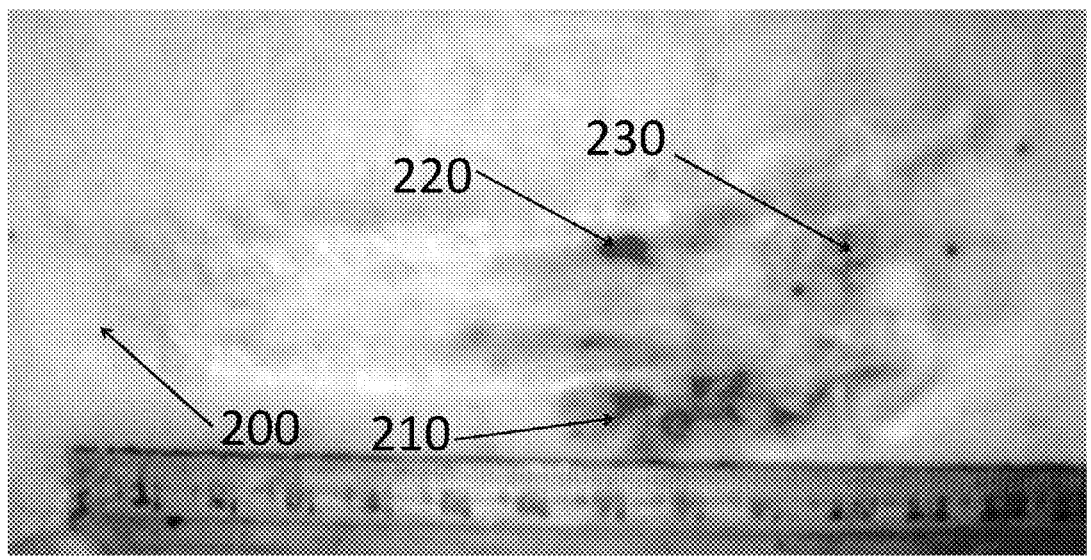
FIG. 2 is an exemplary photograph of the same keloid as in FIG. 1 that has been completely covered with flurandrenolide tape.

A large keloid that was an object of a method of treating and managing as disclosed herein is shown in FIG. 1. In an embodiment, a treatment method began in about 2006-2007. FIG. 2 exemplifies a step of covering the keloid with flurandrenolide tape. The flurandrenolide tape is attached to the keloid firmly as shown in FIG. 2. In an embodiment, flurandrenolide Tape USP is sold by prescription as brand Name, CORDRAN® (flurandrenolide) tape, containing 4 mcg per sq. cm. flurandrenolide (Watson). For example cordran tape is available as large roll (200 cm×7.5 cm). In an embodiment, the CORDRAN® (flurandrenolide) tape may be cut by scissors to sizes that fit a keloid's shape and attached to a surface of the keloid using an adhesive side of flurandrenolide tape. Typically, the tape will stay firmly stuck to the keloid until forcibly peeled off. FIG. 2 is an example of a keloid that has been covered with CORDRAN® (flurandrenolide) tape (brand name, Watson). In this instance, the tape 200 is attached to the keloid by tailoring small, cut pieces to fit the size and shape of the keloid. Each cut piece of the CORDRAN® flurandrenolide tape is attached to the keloid using an adhesive side of the tape. As constructed by the manufacturer of the tape (Watson), the adhesive side also contains the medicine flurandrenolide (generic name). In an embodiment shown in FIG. 2, the keloid displays extremely reddish areas, particularly in an area that is an oldest region 210, which is an origin of the keloid. Other areas in FIG. 2, particularly for example, 220 and 230, are also extremely reddish in appearance. Other additional areas of reddish spotted areas can also be seen in FIG. 2. The reddish color indicates areas of manifestation of irritation, itchiness and pain over many years. The flurandrenolide is a topical corticosteroid known in the literature to be used to suppress irritation and pain. The CORDRAN® (flurandrenolide) tape 200 besides delivering flurandrenolide to the affected areas also provides the added advantage of protecting the keloid against irritation caused by abrasive contact with clothing. In a further embodiment, the flurandrenolide (or Cordran) tape is allowed to stay on the keloid all day while a patient is going about his or her daily business. In a different embodiment, flurandrenolide may be applied to the keloid as a topical cream or jelly or ointment or liquid or a semi-solid or solid (such as powered or granules).

In an embodiment, a method of treating or managing a keloid includes firstly removing flurandrenolide tape (or CORDRAN® (flurandrenolide) tape) by peeling it off the keloid and secondly, cleaning the keloid with water and soap, and then drying the keloid with a cloth or a paper towel. After the keloid is dried, graphites ointment is applied in a manner that includes completely or partially covering the keloid with the graphites ointment. Graphites 6C ointment is available in the open market, for example, sold on the interne by a number of companies such as Pomade, Nelson, Boiron, or SBL. In an embodiment, graphites 10% by weight, in an inactive base comprising petroleum jelly ointment is evenly applied on the keloid and the applied area of the skin is massages gently with digit finger to allow the ointment to soak into the keloid. In an aspect of the method of treatment, witch hazel ointment is applied to the keloid evenly on the keloid either separately or together with graphites. Witch hazel (*Hamamelis virginiana*) is available in the open market as a cream, lotion ointment or liquid. In an embodiment, a *Hamamelis* (*Hamamelis virginiana*) 10% by weight, ointment in an inactive base comprising bees wax and solid paraffin was bought over-the-counter is used herein. The *Hamamelis* ointment is allowed to be absorbed by the keloid. In an embodiment, capsaicin cream or ointment is applied to the keloid. Capsaicin, 8-Methyl-N-vanillyl-trans-6-nonenamide) $(CH_3)_2CHCH=CH(CH_2)_4CONHCH_2C_6H_3\text{-}4\text{-}(OH)\text{-}3\text{---}(OCH_3))$ is the active composition or mixture of chili peppers, which are plants belonging to the genus *Capsicum*. Capsaicin may be obtained over-the-counter as for example, Capzasin HP 0.1% capsaicin (brand name CHATTEM Registered Trade mark, by Chattem Inc., TN). Capsaicin is applied on the keloid by gently rubbing or massaging with a digit. The patient may experience intense irritation or pain at the site of the keloid for a period of about 30 minutes following application of capsaicin. Capsaicin is a known irritant of mammalian skin including that of a human. The irritation following application of capsaicin to a keloid is temporary and may stimulate, inter alia, absorption of the graphites and/or witch hazel (*Hamamelis*) ointment that has already been applied on the keloid, as disclosed (vide supra and infra).

In an embodiment, an application of first, witch hazel ointment, secondly graphites or vice versa, may applied to a keloid. In an alternate embodiment, witch hazel ointment may be applied firstly, and secondly graphites ointment and finally capsaicin cream, and the combination may be massaged and rubbed into the keloid and allowed to be absorbed overnight by the keloid. In a further embodiment, a minimum of 5-10 hours of absorption by keloid of witch hazel and graphites and capsaicin is recommended. In yet another embodiment, the daily treatment cycle using witch hazel, graphites and capsaicin is recommended. This daily treatment regimen is carried out for many years in order to achieve desirable results. These desirable results include, inter alia, but not limited to the following symptoms: reduction in thickness of the keloid, softening of the keloidal tissue, reduction in redness and itchiness and irritation, and reduction in pain. It is anticipated that prolonged treatment over the course of many years will reduce the thickness (flattening) of the keloid to the point where it is contiguous or almost contiguous with normal surrounding skin.

Figure 3A:
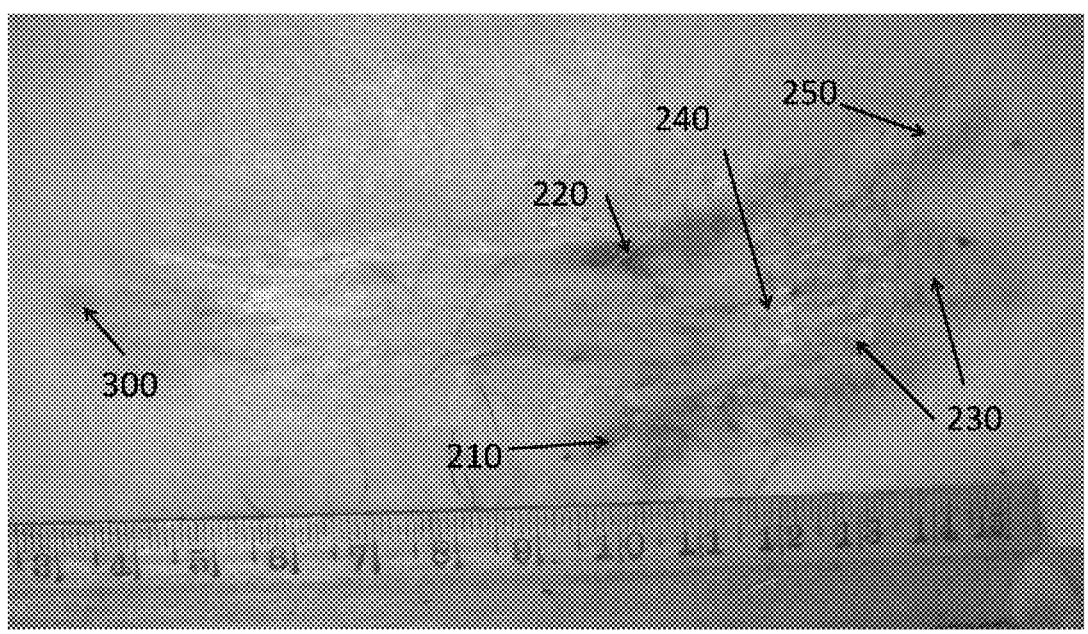
FIGS. 3A and 3B are exemplary close-up-view photograph of the same keloid as in FIG. 1 that has been treated with graphites and witch hazel and capsaicin.
Figure 3B:
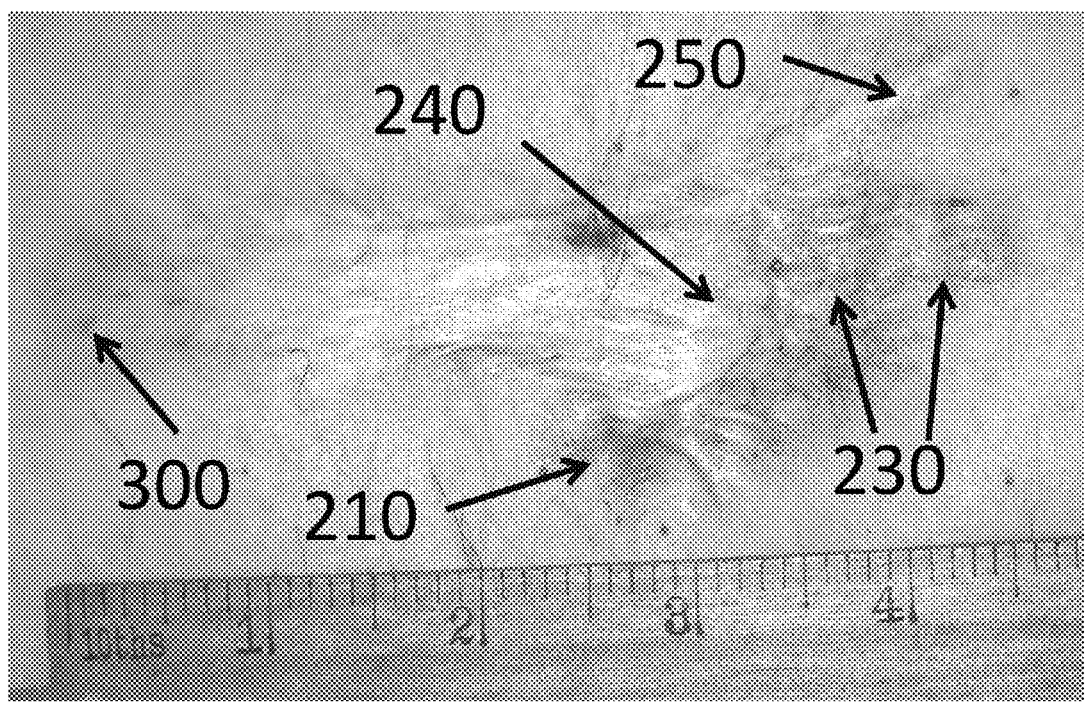

FIG. 3A is a photograph of the same keloid as shown in FIGS. 1 and 2 (see above) that has been treated with a combination of graphites or witch hazel (or both) and capsaicin for over three years. In FIG. 3A, areas denoted 210, 220, and 230 have shown marked improvement in terms decrease in reddish color as a sign of decreased irritation and pain compared to the same areas in FIG. 2. Particularly, area 210 showed a significant reduction in irritation. Note that the area 210 is the origin of the keloid and the oldest and the toughest tissue of the keloid (See above in FIG. 1). Thus there seems to be an improvement as to symptomatic relief following treatment in area 210. Even area 220 showed marked reduction in redness compared to the same area in FIG. 2. But a new reddish spot area 300 appeared. The appearance of new reddish spots is known to be common in keloid growth cycle. In addition, area 240 has flattened out considerably in comparison to the same area 80, 30 previously seen in FIG. 1 (see above). FIG. 3B is a photograph of the same keloid after about five years of treatment with a combination of graphites or witch hazel (or both) and capsaicin. Comparison of FIG. 3A and 3B, reveals that the keloid appears to have further flattened out and there appears to be an overall decrease in thickness as seen in FIG. 3B. For example, areas 230, 240 and 250 appear to be flatter than the corresponding areas in FIG. 3A and FIG. 1. The finger-like 250 appears flatter and less reddish than the corresponding area 250 in FIG. 3A. Likewise, area 210 is flatter in FIG. 3B than in FIG. 3A. Area 230 is also considerably improved as shown in FIG. 3B compared to the same region 230 in FIG. 3A in the sense that it is flatter and less reddish. Area 300 in FIG. 3B is less reddish and less irritated than in FIG. 3A.

Figure 4:
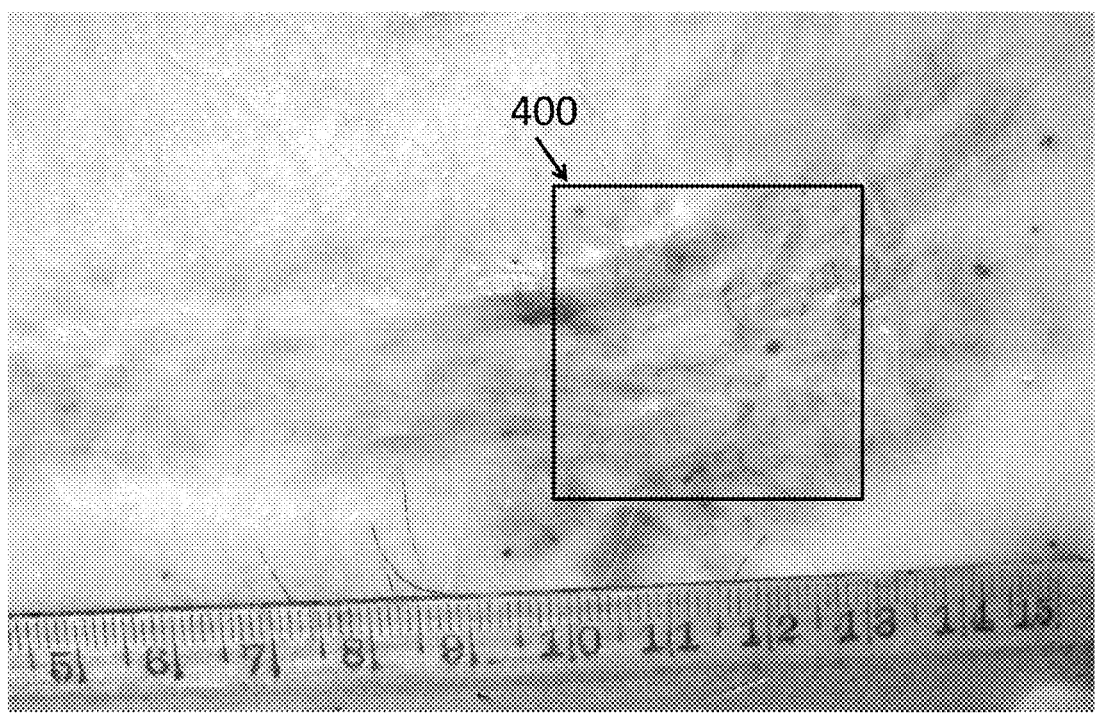
FIG. 4 is an exemplary close-up photograph of the same keloid as in FIG. 1 that has been treated with graphites and witch hazel and capsaicin.
Figure 5:
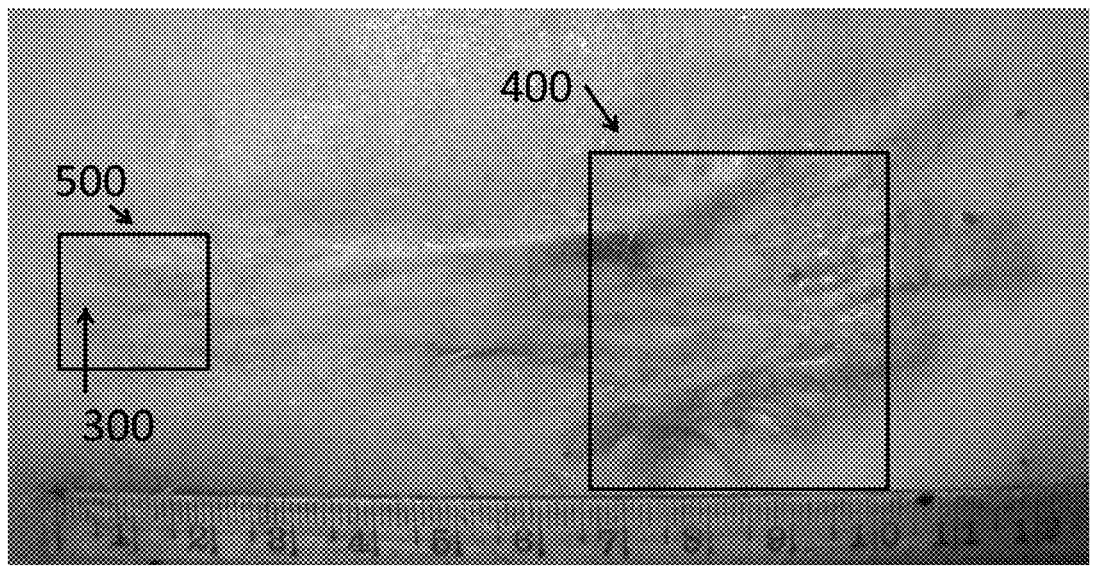
FIG. 5 is an exemplary close-up photograph of the same keloid as in FIG. 1 that has been treated with graphites and witch hazel and capsaicin.

FIG. 4 is an exemplary close-up view of the same keloid disclosed above. FIG. 4 shows a view of the keloid treatment for about three to four year as disclosed herein. The thickest and the most fibrous region of the keloid and is shown in the square box denoted 400. By toughness it is meant to the ordinary touch and feel with human fingers. This region also comprises the early and older growth area of the keloid. After 3-4 years of treatment with methods disclosed herein, as seen in FIG. 5, there has been a marked improvement compared to the same region 400 as seen in FIG. 4. In terms of reduction in overall redness and decrease in thickness of region 400, the treatment has had a positive effect. Furthermore, for example a red spot area 300 almost disappeared (Compare FIG. 3 with FIG. 4).

TABLE I

Characteristics of keloid's origin area 400 as shown in FIGS. 4 and 5

| Year | Thickness (mm) | Redness/Irritation (0-10) (arbitrary scale 0-10) |
|------|----------------|--------------------------------------------------|
| 2007 | ~3             | 8                                                |
| 2008 | <3             | 7                                                |

TABLE I-continued

Characteristics of keloid's origin area 400 as shown in FIGS. 4 and 5

| Year | Thickness (mm) | Redness/Irritation (0-10) (arbitrary scale 0-10) |
|---|---|---|
| 2009 | ~2 | 6 |
| 2010 | <2 | 4 |
| 2011 | ~1 | 3 |
| 2012 | <1 | 2 |

In an embodiment, TABLE 1 is an example of a record of changes in a thickness of a keloid as illustrated in FIGS. 1-5. Approximate thickness was measured in a boxed region 400 (FIGS. 4 and 5). In 2007 the keloid had an approximate thickness of about 3 mm, measured from base of normal skin to the thickest area 400. Every year since then the approximate thickness decreased, and in 2012 it was approximately 1 mm or less, which amounts to approximately 60% reduction from its original thickness. Likewise, as exemplified in TABLE 1, the redness and irritation that were characteristic of the area 400 (FIGS. 4 and 5) as also decreased as indicated on an arbitrary scale (0-10) by visual examination. Similarly, as exemplified in TABLE II, the thickness was measured in the most nascent area of the keloid as illustrated in FIG. 5 in the box 500. As illustrated in TABLE II, there was approximately 80-90% reduction in the thickness going down from about 2 mm to about less than 0.2 mm (measurements are approximate).

TABLE II

Characteristics of keloid's most nascent area # 300

| Year | Thickness (mm) | Redness/Irritation (arbitrary scale 0-10) |
|---|---|---|
| 2007 | ~2 | 5 |
| 2008 | <2 | 4 |
| 2009 | ~1 | 4 |
| 2010 | <1 | 3 |
| 2011 | <~0.5 | 2 |
| 2012 | <~0.2 | 1 |

This reduction is more than the reduction that was seen in thickness of the oldest region 400 (FIG. 5), which is consistent with the knowledge of those skilled in the art that the more nascent growth areas of a keloid are softer and more responsive to treatment.

EXAMPLE 2

Figure 6:
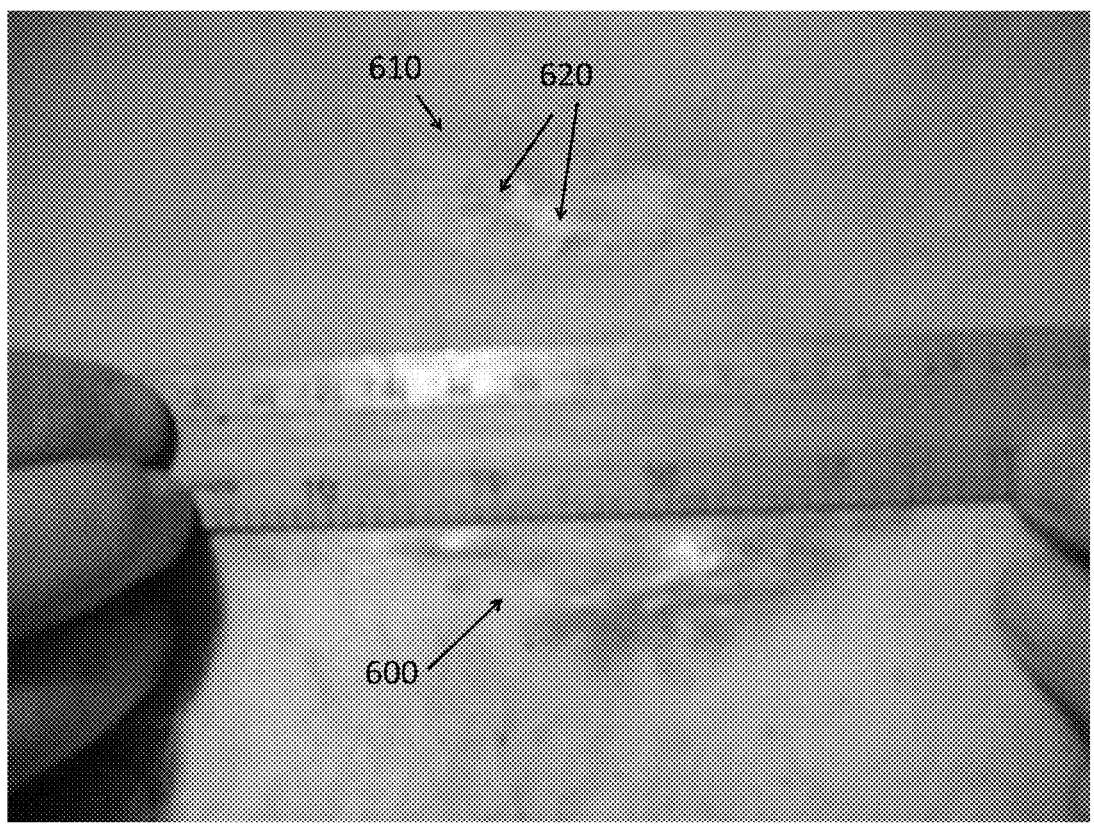
FIG. 6 is an exemplary photograph of a smaller keloid growth above the larger keloid as shown in FIG. 1.
Figure 7:
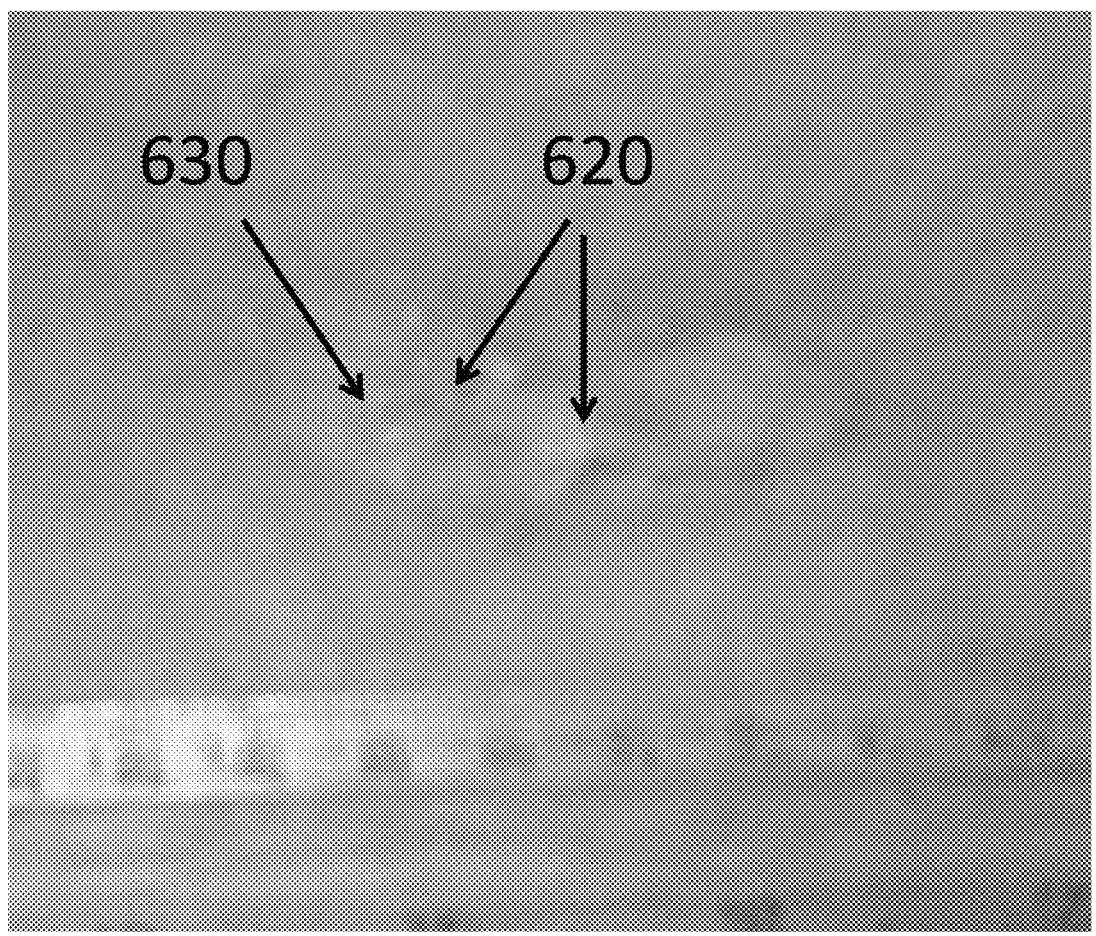
FIG. 7 is an exemplary close-up view photograph of the smaller keloid growth as in FIG. 6.
Figure 8:
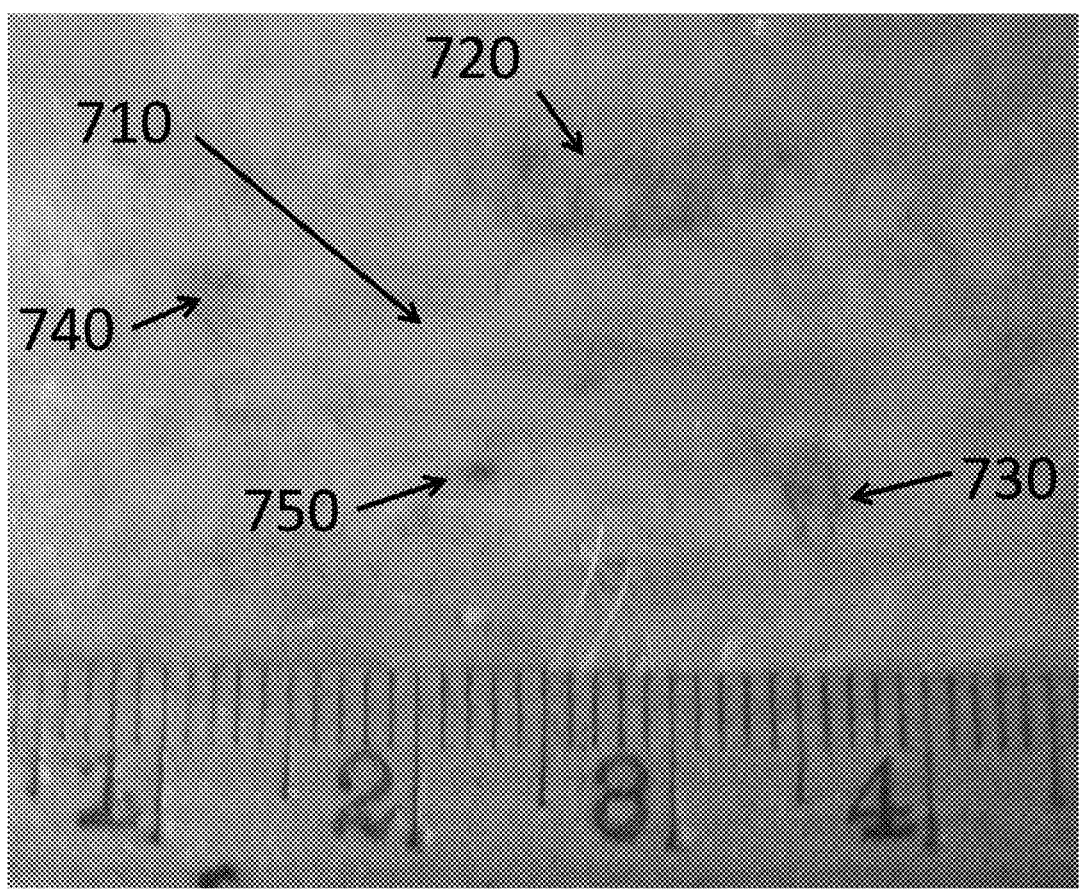
FIG. 8 is an exemplary close-up view photograph of the smaller keloid growth as in FIG. 7 that has been covered with flurandrenolide tape.
Figure 9:
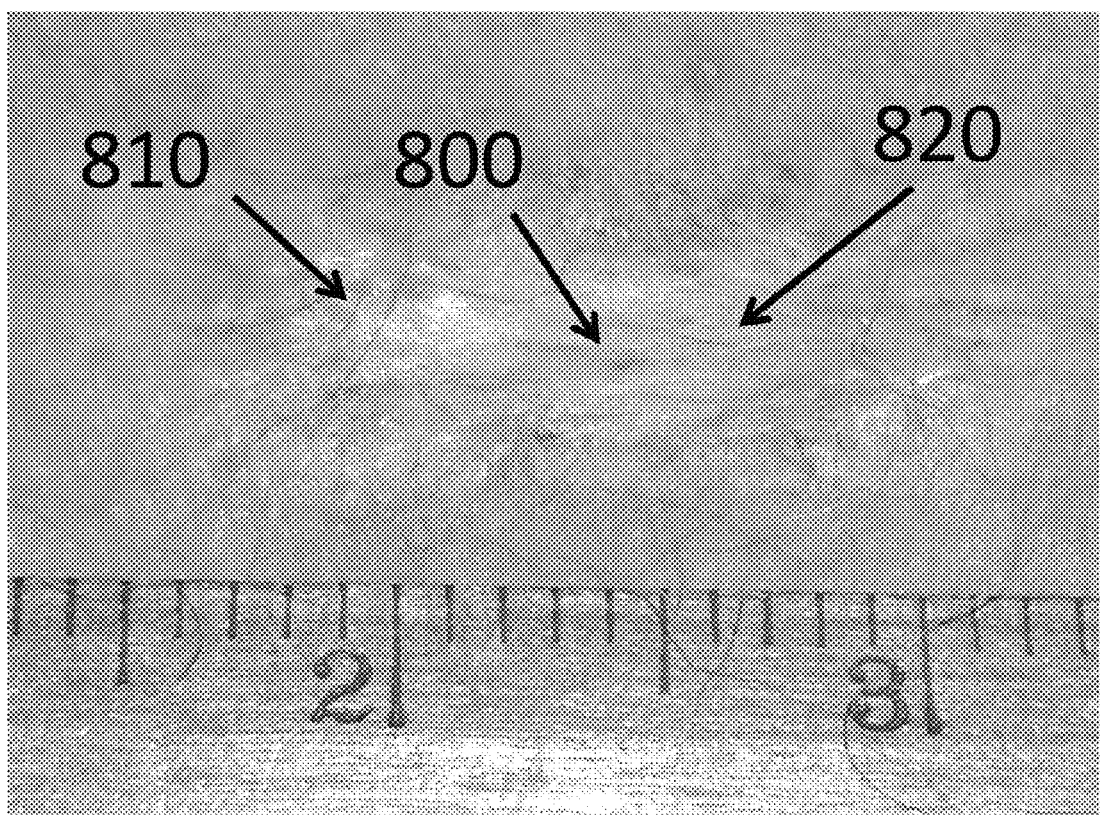
FIG. 9 is an exemplary close-up view photograph of the smaller keloid growth that has been treated with graphites and witch hazel and capsaicin for more than 5 years.

In an embodiment, FIG. 6 is an illustrative example of a second, albeit smaller, keloid growth 610 in a vicinity of a major keloid 600 that was disclosed vide supra (FIGS. 1-5). The smaller keloid is located just below the neck on a human chest area. The smaller keloid 610 appeared about 15 years after the major keloid 600. Those skilled in the art recognize that smaller and less pronounced keloid growth may occur in the vicinity of major/large keloids. FIG. 6 also discloses raised areas 620 with the smaller keloid 610. These raised areas are characterized by ridges 620, and striations 630, as illustrated in a close-up view in FIG. 7. Areas 620 and 630 that were particularly itchy and painful while rubbing against clothing, for instance. In addition, as illustrated in an embodiment in FIG. 8, the smaller keloid showed reddish areas numbered 720, 730, 740 and 750. These reddish areas are typically irritated and itchy. In an embodiment, this keloid was treated as disclosed above, by first covering it with CORDRAN® (flurandrenolide) tape 710 for over 10 hours and then removing the tape, followed by treatment methods as disclosed above. In an embodiment, he method of treatment, included application of witch hazel ointment (10% by mass or weight) and graphites (10% by mass (or weight)) ointment and by Capsaicin (0.1% by mass (or weight)). In an embodiment, the above treatment was administered on a daily basis for over 4 years. As illustrated in FIG. 9, the keloid showed improvement in appearance and was flattened to a significant extent. Some of ridge area 800 was greatly flattened and the previously striated area 810 was smoothened out. There was at least 60-70% reduction in thickness. The reddish area 820 also showed good response. Overall the keloid was less itchy compared to before treatment.

Figure 10:
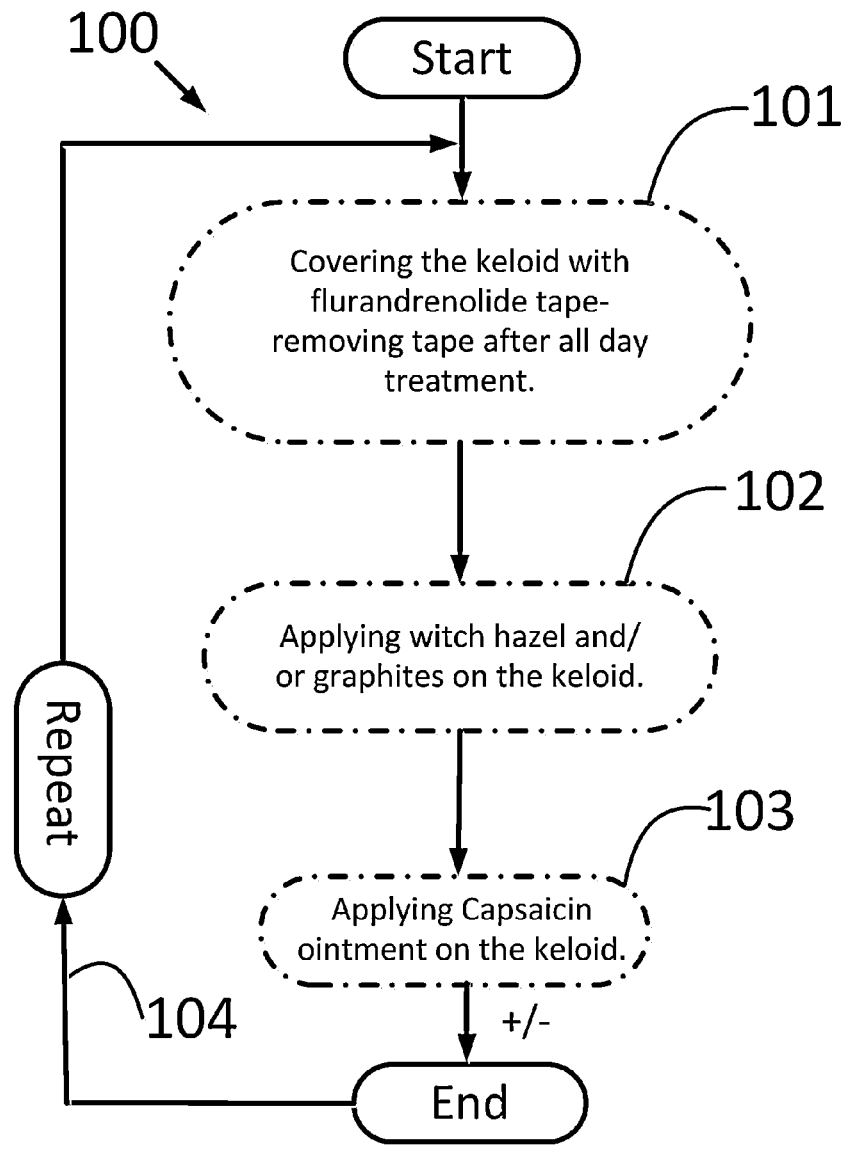
FIG. 10 is a schematic of a method of treating a keloid.

FIG. 10 illustrates a schematic of various steps in an embodiment 100 of a method of treating a keloid in a mammal. The method comprises a step 101 of covering the keloid with flurandrenolide tape and removing the tape after all day treatment; and a step 102 of applying witch hazel and/or graphites ointment on the keloid; and a step 103 of applying capsaicin ointment on the keloid. In a further embodiment, the steps recited above may be executed successively or in one or more steps (+/− in FIG. 10) and the steps are repeated 104 until the keloid is reduced in thickness and size and to a level of comfort for the patient.

Figure 11:
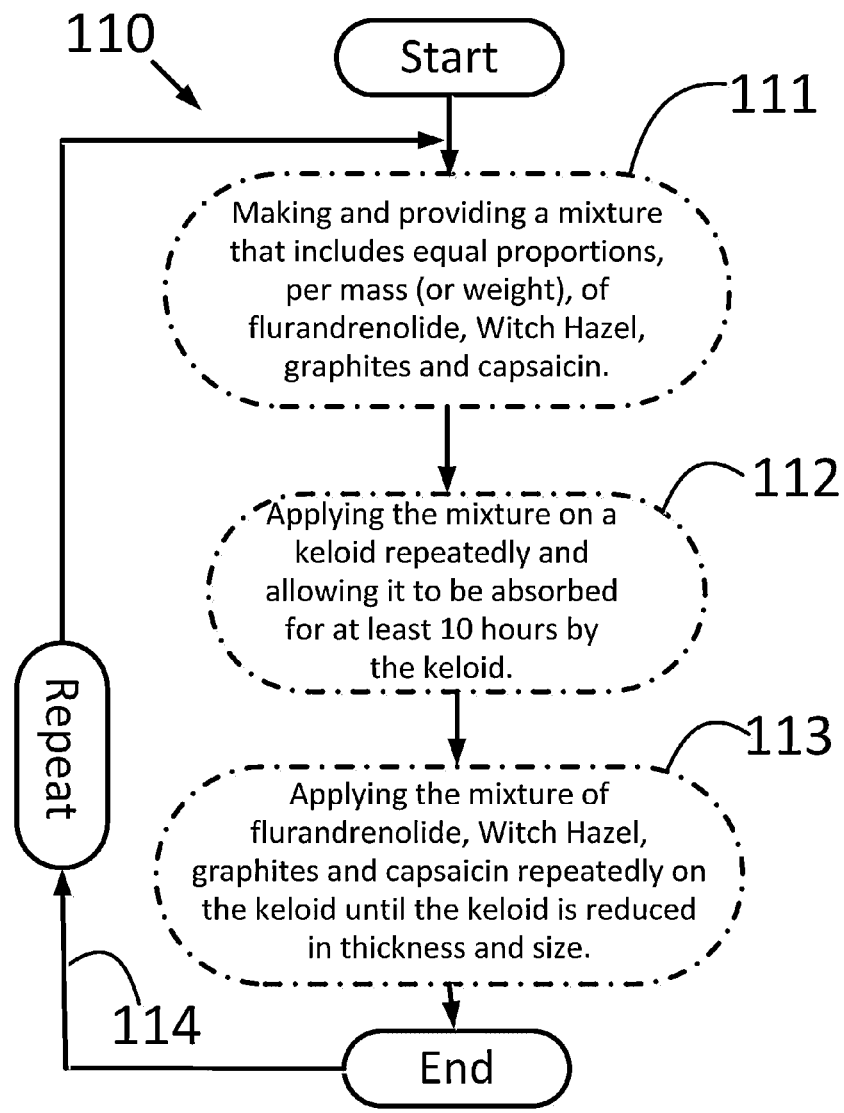
FIG. 11 is a schematic of a method of treating a keloid.

FIG. 11 illustrates a schematic of steps in an embodiment 110 of a method of treating a keloid in a mammal. The method comprises a step 111 of first making and providing a mixture that includes equal proportions, per mass (or weight), of flurandrenolide, witch hazel, graphites and capsaicin; and secondly, the step 112 of applying the mixture on a keloid repeatedly and allowing it to be absorbed for at least 10 hours by the keloid. In yet another embodiment, the method includes the step 113 of applying the mixture of flurandrenolide, witch hazel, graphites and capsaicin repeatedly on the keloid until the keloid is reduced in thickness and size. The method further includes applying the mixture of flurandrenolide, Witch Hazel, graphites and capsaicin to the keloid until the keloid is reduced to a level of a comfort for a mammal. The above steps are repeated until satisfactory results are achieved 114.

As used herein, the term "ointment" includes, but is not limited to any suitable pharmaceutical formulation such as a viscous substance, preparation, unction, spreadable substance, oil, cosmetic, unguent, emollient, or medicament; a salve, paste, ointment, jelly, cream, thick or semi-solid, liquid, gaseous form thereof that comprises a mixture or combination of active and/or inactive ingredients disclosed herein.

As used herein, the terms "absorbed" or "absorb" or "soak" includes, but is not limited to, passive or active diffusion of a substance into a keloid, impregnation, imbibition, penetration, covering, take in or soak up (energy, or a liquid or other substance) by chemical or physical action, typically gradually.

As used herein the term "cover", "covering" or "covered" or the like, includes, but is not limited to putting any medicinal or chemical ingredient described herein or flurandrenolide or CORDRAN® (flurandrenolide) tape, such as on top of keloid or in front of keloid in order to completely or partially cover or protect or conceal it.

As used herein, the terms "rubbing" or "massaging" with finger includes but is not limited to, the action of contacting a keloid with a human or mammalian digit from an arm or hand and applying pressure on the keloid that is contacted by the digit, and moving the digit over the keloid either rapidly or slowly such as in a back and forth movement.

General Comments and Observations

Embodiments of method of treating a keloid in a mammal have been disclosed herein. This method of treating keloids is a long-term treatment method that is practiced over many years. Typically, good results may be seen after one-year of treatment, depending on the age and the extent of collagenization of a keloid. Those skilled in the art recognize that, in general, the older a keloid is the more difficult it is to treat effectively and that more nascent growth areas in a keloid are more susceptible to treatment. The method disclosed herein is not a cure. It is a method that treats the keloid and manages pain, redness and irritation, itchiness, and the treatment attempts to reduce unsightliness by flattening the keloid. The invention may not reduce the overall length and breadth of a keloid but results are more towards reduction in the overall thickness of the keloid. In one aspect of the treatment method, best results were seen with nascent growth areas of the keloid that were reduced in thickness to co-equalization of the keloid level to that of the surrounding unaffected areas of the skin.

The foregoing detailed description has set forth various embodiments of the methods and/or treatments via the use of photographs, tables and examples. Insofar as such photographs, tables and examples contain one or more steps or methods, it will be understood by those skilled in the art that each component or method or step within such photographs, tables and example can be implemented, individually and/or collectively, by a wide range of any combination thereof. One skilled in the art will recognize that the herein described methods, protocols or compositions or mixtures or steps and objects and the discussion accompanying them are used as examples for the sake of conceptual clarity and that various methods, modifications are within the skill of those in the art. Consequently, as used herein, the specific examples or embodiments set forth and the accompanying general comments and observations are intended to be representative of their more general classes. In general, use of any specific exemplar or embodiment herein is also intended to be representative of its class, and the non-inclusion of such specific steps, examples, embodiments or photographs, tables and examples or the like herein shall not be taken as indicating that limitation is desired. The herein described subject matter sometimes illustrates different compositions or mixtures comprised within, or associated with, different or other composition(s) or mixtures. It is to be understood that such described composition or mixtures, compositions, photographs, tables and examples are merely exemplary, and that in fact many other photographs, tables and examples can be implemented, which achieve the same or similar treatment results. In a conceptual sense, any treatment method or protocol to achieve the same treatment result is effectively "equivalent" to this disclosure such that the desired treatment result is achieved. Hence, any two methods or steps herein combined to achieve a particular treatment result can be seen as "equivalent" to each other such that the desired treatment result is achieved, irrespective of differences in composition(s) or mixtures or steps. Likewise, any two composition(s) or mixtures or steps so equivalent can also be viewed as being "functionally "equivalent", to each other to achieve a desired treatment result, and any two compositions or mixtures capable of being so associated can also be viewed as being capable of acting together, with each other to achieve a desired treatment result.

One skilled in the art will recognize that the herein described composition(s) or mixtures, and methods (e.g., steps), materials and the discussion accompanying them are used as examples for the sake of conceptual clarity and that various modifications and variations are within the skill of those in the art. Consequently, as used herein, the specific example set forth and the above detailed discussion are intended to be representative of their more general classes. In general, use of any specific example or embodiment herein is also intended to be representative of its class, and the non-inclusion of other composition(s) or mixtures or methods (or steps) and materials herein should not be construed as indicating that a limitation is desired.

With respect to the use of substantially any plural and/or singular terms herein, those having skill in the art can transmute from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the embodiments herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions comprising only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B".

I claim the following:

1. A method of treating a keloid in a human consisting of the steps of:
    (a) covering the keloid with flurandrenolide tape; and
    (b) removing the flurandrenolide tape from the keloid after at least 5 to up to 10 hours; and
    (c) cleaning the keloid with soap and water and drying the keloid; and
    (d) applying graphites ointment on the keloid wherein the graphites ointment consists of graphites in an inactive base; and
    (e) applying witch hazel ointment on the keloid wherein the witch hazel ointment consists of witch hazel in an inactive base; and
    (f) applying capsaicin cream on the keloid wherein the capsaicin cream consists of capsaicin in an inactive base; and
    (g) allowing the graphites, witch hazel, and capsaicin to be absorbed by the keloid for at least 10 hours; and
    (h) cleaning the keloid with soap and water and drying the keloid; and
    (i) repeating the above steps daily.

2. A method of treating a keloid in a human consisting of the steps of:
    (a) making a mixture in an inactive base wherein the mixture consists of equal proportions by weight of flurandrenolide, witch hazel, graphites and capsaicin; and
    (b) applying the mixture on the keloid in a manner that includes covering the keloid; and
    (c) allowing the mixture to be absorbed by the keloid for at least 10 hours; and
    (d) cleaning the keloid with soap and water and drying the keloid; and
    (e) repeating the above steps daily.

* * * * *